US010152453B1

(12) United States Patent
Matz

(10) Patent No.: US 10,152,453 B1
(45) Date of Patent: Dec. 11, 2018

(54) SYSTEM AND METHOD FOR MANAGING MEDICAL PRESCRIPTIONS AND INVENTORY

(75) Inventor: William R. Matz, Atlanta, GA (US)

(73) Assignee: AT&T INTELLECTUAL PROPERTY I, L.P., Atlanta, GA (US)

( * ) Notice: Subject to any disclaimer, the term of this patent is extended or adjusted under 35 U.S.C. 154(b) by 1974 days.

(21) Appl. No.: 10/611,601

(22) Filed: Jun. 30, 2003

(51) Int. Cl.
*G06Q 50/22* (2012.01)
*G06F 17/00* (2006.01)
*G06F 17/30* (2006.01)

(52) U.S. Cl.
CPC .............. *G06F 17/00* (2013.01); *G06F 17/30* (2013.01)

(58) Field of Classification Search
CPC ........ G06Q 50/24; G06Q 50/22; G06F 17/00; G06F 17/30
USPC ....................................................... 705/2, 3
See application file for complete search history.

(56) References Cited

U.S. PATENT DOCUMENTS

| | | | |
|---|---|---|---|
| 3,597,742 A | 8/1971 | Philipps | |
| 4,835,372 A | 5/1989 | Gombrich | |
| 4,857,716 A | 8/1989 | Gombrich | |
| 4,967,928 A | 11/1990 | Carter | |
| 5,065,315 A * | 11/1991 | Garcia | G06Q 50/22 |
| | | | 705/2 |
| 5,536,084 A | 7/1996 | Curtis et al. | |
| 5,732,401 A | 3/1998 | Conway | |
| 5,737,539 A | 4/1998 | Edelson | |
| 5,758,095 A | 5/1998 | Albaum et al. | |
| 5,781,442 A | 7/1998 | Engleson et al. | |
| 5,807,336 A | 9/1998 | Russo et al. | |
| 5,822,544 A * | 10/1998 | Chaco | G06F 19/3418 |
| | | | 705/2 |
| 5,867,821 A * | 2/1999 | Ballantyne | G06Q 10/10 |
| | | | 705/2 |
| 5,924,074 A * | 7/1999 | Evans | G06F 19/325 |
| | | | 705/3 |
| 5,960,085 A | 9/1999 | De la Huerga | |

(Continued)

OTHER PUBLICATIONS www.fredmeyer.com The Kroger Company. 2002.*

(Continued)

*Primary Examiner* — Robert W Morgan
*Assistant Examiner* — Kristine Rapillo
(74) *Attorney, Agent, or Firm* — Scott P. Zimmerman, PLLC

(57) ABSTRACT

Systems and methods for managing patient information on a primary computer system involving the creation of an electronic patient chart; receiving updated information to the patient chart; and automatically accessing a secondary system based on the updated information. The primary and secondary computer systems communicate to better manage inventory, medical prescriptions and other administrative concerns. When the patient chart is edited by a healthcare professional, the primary computer system evaluates the updated information and then sends requests to one or more secondary systems automatically. The updated information may involve the need for a new medicine for the patient, a new appointment for the patient to be set up, and/or a new bill to be generated for the patient, among others. The secondary system or systems provide back-end management for these requests. Such back-end management occurs relatively automatically and substantially in real time.

11 Claims, 12 Drawing Sheets

(56) References Cited

U.S. PATENT DOCUMENTS

| | | | |
|---|---|---|---|
| 6,021,392 A * | 2/2000 | Lester | G06F 19/326 |
| | | | 705/2 |
| 6,139,495 A | 10/2000 | De La Huerga | |
| 6,322,502 B1 | 11/2001 | Schoenberg et al. | |
| 6,381,576 B1 | 4/2002 | Gilbert | |
| 6,705,990 B1 | 3/2004 | Gallant et al. | |
| 7,343,565 B2 * | 3/2008 | Ying | G06F 3/0482 |
| | | | 715/780 |
| 2002/0042725 A1 | 4/2002 | Mayaud | |
| 2002/0145534 A1 | 10/2002 | Dempsey | |
| 2003/0050802 A1 | 3/2003 | Jay et al. | |
| 2003/0055685 A1 * | 3/2003 | Cobb | A61M 5/172 |
| | | | 705/3 |
| 2003/0083903 A1 * | 5/2003 | Myers | G06F 19/324 |
| | | | 705/2 |
| 2003/0154110 A1 | 8/2003 | Walter et al. | |
| 2003/0160698 A1 | 8/2003 | Andreasson et al. | |
| 2003/0206116 A1 | 11/2003 | Weiner et al. | |
| 2003/0236683 A1 | 12/2003 | Henderson et al. | |
| 2004/0010425 A1 * | 1/2004 | Wilkes | A47B 81/00 |
| | | | 705/3 |
| 2004/0172284 A1 | 9/2004 | Sullivan | |
| 2004/0172295 A1 | 9/2004 | Dahlin et al. | |
| 2004/0193449 A1 * | 9/2004 | Wildman | G06Q 50/22 |
| | | | 705/2 |
| 2008/0281637 A1 | 11/2008 | Matz | |

OTHER PUBLICATIONS

"The potential role of computerization and information technology in improving prescribing in hospitals." H.-J. Guchelaar, M.D. Kalmeijer. Pharmacy World & Science. Dordrecht: Jun. 2003. vol. 25, Issue 3, p. 83.

"Computerized prescribing: Building the electronic infrastructure for better medication usage." Gordon D Schiff, T Donald Rucker. JAMA. Chicago: Apr. 1, 1998. vol. 279, Issue 13, p. 1024-1029.

* cited by examiner

SYSTEM AND METHOD FOR MANAGING MEDICAL PRESCRIPTIONS AND INVENTORY

FIELD OF THE INVENTION

The present invention relates to the medical industry and, in particular, to methods of managing patient records. More particularly, the present invention relates to the manner in which patient records are contemporaneously updated during actual patient care activities. More particularly still, the present invention relates to methods and systems for providing additional inventory and administrative services during a patient visit.

BACKGROUND OF THE INVENTION

During a typical office visit to a physician or other medical professional (hereinafter "healthcare professional"), whether in an office or a hospital, a separate patient chart is created for each new patient. This chart lists all the relevant information related to that patient such as medical history and specific medical needs. The chart typically includes other pertinent information such as the patient's personal identification information such as their name, address, billing information, emergency contact, etc. Indeed, the chart is the primary document maintained in most medical arenas. During subsequent visits this chart is pulled and handed to the healthcare professional for contemporaneously taking notes and making a record of discussions and advice given to the patient. The chart also typically contains information related to prescriptions written by the healthcare professional during particular visits. Since the chart is in paper form, it is handed back and forth between assistants and secretaries as part of the patient care process. Furthermore, such a chart may be handed to or passed through the accounting department for proper insurance and patient billing.

Significant drawbacks related to these paper charts are encountered on a daily basis in numerous healthcare facilities. For example, charts are often lost or misplaced. A lost or misplaced chart creates a very difficult situation because the re-creation of such information is nearly impossible. Other times the situation may be time critical such that re-creation of the information would simply take too long. Thus, a lost chart is not only time consuming but potentially dangerous as well.

Another significant problem associated with the paper charts relates to the legibility of the handwritten notes. Indeed, failure to accurately read a medical chart may result in the improper prescription of certain drugs, which can be very dangerous. Double-checking such issues requires the transfer of the paper chart to another person for verification.

In other situations, such as where a nurse is caring for a patient in a hospital environment, the doctor in charge may want or need to understand the status of the patient. In order to do so, the doctor must either call or talk to the attending nurse or physically go to the location of the patient's chart (which is typically in or near the room in which the patient is staying), and examine the chart in person. This is unsatisfactory in many cases when the nurse cannot be reached and the doctor is far from the hospital or the particular patient.

Furthermore, although not often recognized as a problem, the paper charts may in fact aid in the transmission of diseases as the charts are reused and passed from room to room without disinfection. The inadvertent transmission of diseases is, of course, a dangerous situation.

Yet another drawback associated with paper patient charts relates to the difficulties in handling administrative tasks when dealing with a paper chart. For example, when a healthcare professional prescribes a certain medication, a nurse often assesses whether the medication is on-hand, especially in a hospital environment. In such a case, the nurse typically must decipher the handwriting on the chart and then manually examine the inventory, whether the inventory is managed electronically or not. That is, even if the inventory is stored and maintained on a computer system, that system must still be accessed and checked by the nurse in order to determine whether the medicine is on-hand. Given the potential for error in reading the handwriting or managing the inventory, the present system using paper patient charts is unsatisfactory.

These problems all directly impact the safety and satisfaction of patients and the care that they are given and it is with respect to these and other considerations that the present invention has been made.

SUMMARY OF THE INVENTION

The present invention relates to a computerized patient chart system that involves a patient room computer system for the contemporaneous display and maintenance of patient medical information, i.e., edits and additions to the patient chart. In accordance with other aspects of the present invention, the patient room computer system is connected, via a network, to a primary computer system. Further, the primary computer system is connected to one or more secondary systems. The primary and secondary computer systems communicate to better manage inventory, medical prescriptions and other administrative concerns. When the patient chart is edited by a healthcare professional, the primary computer system evaluates the updated information and then sends requests to one or more secondary systems automatically. The updated information may involve the need for a new medicine for the patient, a new appointment for the patient to be set up, and/or a new bill to be generated for the patient, among others. The secondary system or systems provide back-end management for these requests. Such back-end management occurs relatively automatically and substantially in real time.

In accordance with certain aspects, the present invention relates to systems and methods for managing patient information on a primary computer system. The invention involves the creation of an electronic patient chart; receiving updated information to the patient chart; and automatically accessing a secondary system based on the updated information. In an embodiment, the updated information to the patient chart relates to a prescription for medicine and wherein the act of accessing a secondary system involves requesting inventory information from an inventory system regarding the prescribed medicine; receiving said inventory information; and displaying the received inventory information, thereby allowing a healthcare professional to act or react to the received inventory information. With respect to one embodiment, the secondary system is an inventory database system for managing inventory of medicine located on the primary computer system. With respect to another embodiment, the secondary system is an inventory database system for managing inventory of medicine on a separate computer system located in a separate pharmacy. Indeed the pharmacy may be in a remote location such that the secondary computer system communicates with the primary computer system over the Internet.

With respect to other aspects, when the updated information relates to a medical prescription for medicine, the invention involves requesting a pharmacy to fill the prescription and in response to the request to fill, the primary computer system receives information regarding the availability of the medicine and if available, price information and/or pickup times. Upon receiving information regarding availability, if the medicine is not available, the primary computer system may receive information regarding other pharmacy locations having the medicine. If the patient has insurance that pays for some medicine, the invention further relates to automatically determining whether patient insurance covers the prescribed medicine and notifying the healthcare professional if insurance does not cover the prescribed medicine.

With respect to other aspects, the secondary system may relate to an electronic billing system. The billing system being contacted when updated information indicates that a new bill should be generated and sent to the patient and/or the patient's insurance company. Consequently, the invention involves determining that the updated information requires that the patient receive a new bill; and automatically requesting the secondary system begin the billing process. The secondary system may automatically determine whether the patient insurance covers the new bill and may further notify the healthcare professional if the insurance does not cover the new bill.

In yet another embodiment, the secondary system may relate to an electronic scheduling system. The scheduling system being contacted when the updated information indicates that a new appointment should be made.

The invention may be implemented as a computer process, a computing system or as an article of manufacture, such as a computer program product. The computer program product may be a computer storage medium readable by a computer system and encoding a computer program of instructions for executing a computer process. The computer program product may also be a propagated signal on a carrier readable by a computing system and encoding a computer program of instructions for executing a computer process.

A more complete appreciation of the present invention and its improvements can be obtained by reference to the accompanying drawings, which are briefly summarized below, to the following detailed description of presently preferred embodiments of the invention and to the appended claims.

DETAILED DESCRIPTION

Figure 1:
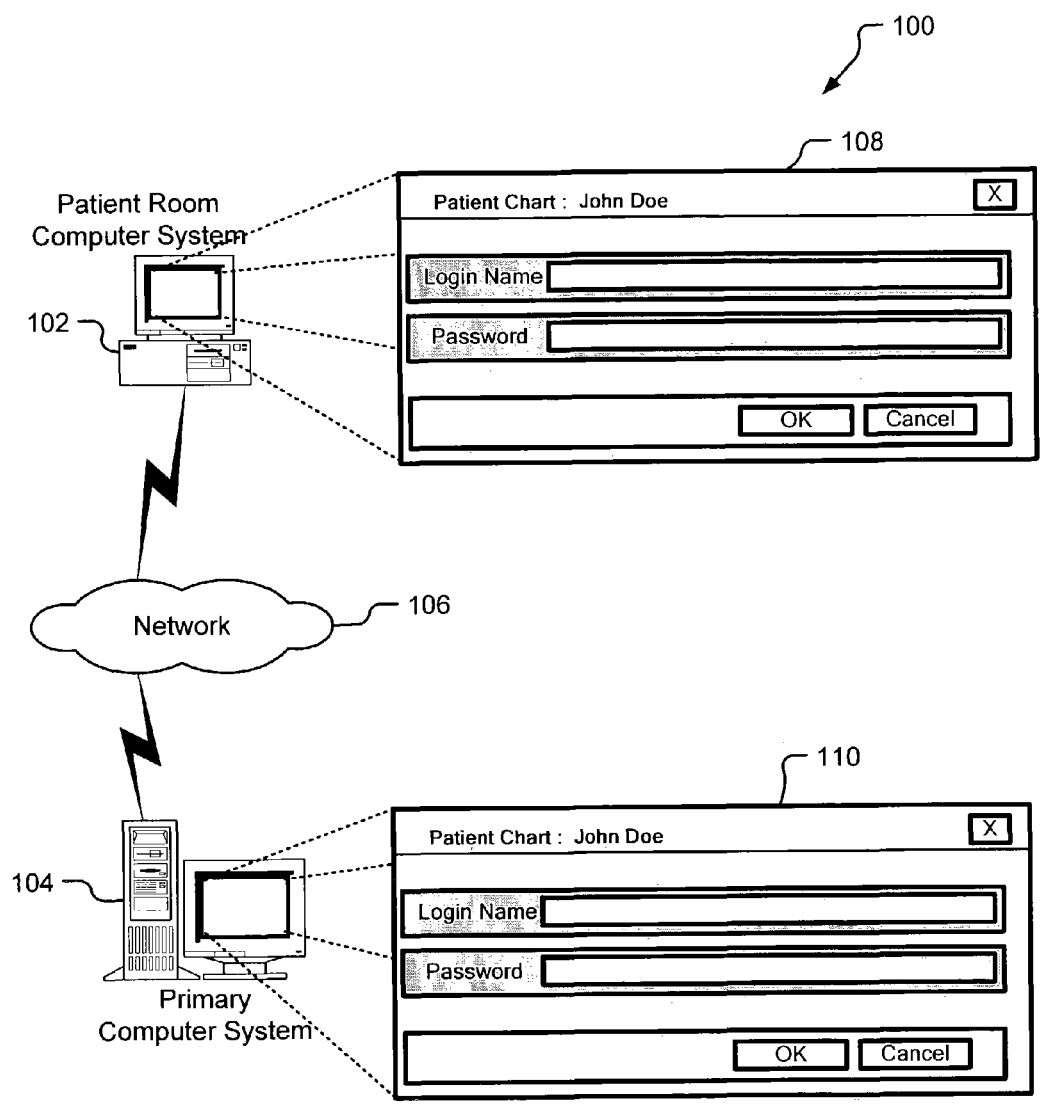
FIG. 1 is a block diagram illustrating the environment for the present invention including a networked system for entering and managing patient information.

The present invention relates to a computerized network in a healthcare environment. A distributed environment 100 incorporating aspects of the present invention is shown in FIG. 1. The environment 100 relates to a distributed network having at least one patient room computer system 102 that communicates with at least one primary computer system 104. The client computer system 102 and the server computer system 104 communicate using a communication protocol over the distributed network 106. In one embodiment, the communication network 106 is an intranet. In other embodiments, the network 106 utilizes the Internet. The patient room computer system 102 is used to display an electronic or computerized version of a patient chart having patient information, and to edit the same, thereby eliminating the need for paper-based patient charts.

The patient room computer system 102 receives and displays data entered by the doctor or other healthcare professional providing patient care to the patient. The system 102 allows the healthcare professional to enter the information contemporaneously with the patient visit, i.e., during or shortly after the patient visits the healthcare professional. Although the healthcare professional typically enters such information, as may be understood, many different individuals may utilize this system to record information related to a particular patient and/or visit, including nurses, administrators, staff employees, etc.

The patient room computer system 102 displays the patient chart for a visiting patient. In an embodiment, the healthcare professional can access the information by connecting to the network 106 and requesting the chart for a particular patient. Access to the chart may require a login name and password to be entered in order to access the patient information. An exemplary login screen for a particular patient, e.g., John Doe, is shown as screen shot 108 in FIG. 1. This login provides security for the patient information as only those persons knowing the login name and password can access the information. Also, as shown in FIG. 1, the patient chart may be accessed from both the patient room computer system 102 and the primary computer system 104. When accessing the patient chart from the system 104, a similar login screen 110 is provided for security purposes.

In another embodiment, such as when the patient room computer 102 is a mobile device, the relevant patient information may be automatically displayed upon entering the patient's room. Alternatively, the login screen may be automatically displayed. However, when the device is a mobile device, some security may be relaxed since it is assumed the holder of the device is authorized to view patient information. Of course, many other known security methods and procedures may be implemented to protect the patient's privacy.

The automatic display of patient chart information upon entering the patient's room may be achieved through relatively constant communication between the device 102 and transmitting/receiving devices (not shown) located in the patient's room and the primary computer system 104. These communications may enable the primary computer system to understand the location of the patient room computer system and hence, which information should be downloaded and displayed on the patient room computer system 102. Alternatively, the patient room computer system may have bar-code reading capabilities. In such a case, the room may have an associated bar-code, such as on door or in some other area of the room. Thus, the healthcare professional need only scan the bar code to identify the room location, transmit the same to the primary computer system 104 to thus receive the relevant patient information. In yet another embodiment, the patient may have an associated bar-code, e.g., printed on a bracelet, and the healthcare professional need only scan this information. In this embodiment, the room location is not relevant, as the primary computer system can download the proper information for the patient independent of where the patient room computer system is located. More details on automatic and semi-automatic downloading or accessing of information can be found in U.S. application Ser. No. 10/611,250, filed Jun. 30, 2003 and entitled "System and Method of Automatically Displaying Patient Information, incorporated herein by reference for all that it discloses and teaches, filed concurrently herewith, and assigned to the Assignee of the present application.

In a particular embodiment of the present invention, when both computer systems 102 and 104 have correctly accessed a patient's chart, the displays are linked and information provided on one system 102 or 104, is substantially simultaneously shown on the other system 104 or 102 respectively. Providing the simultaneous display on the two systems 102 and 104 provides a monitoring capability for the healthcare facility. That is, while a healthcare professional or some other person is entering information related to a patient, another person may monitor the data entry to see if errors occur. As an example, while a healthcare professional enters a prescription for a particular patient, a monitoring nurse can confirm that the prescription is safe for that patient based on known history information regarding allergies, heart conditions, or other predetermined issues.

Also, a person monitoring the data entry may provide improved service to the patient through advanced recognition of special needs such as medical supplies, medicines or future appointments, etc. For example, a nurse monitoring a visit by watching system 104 may recognize that the healthcare professional has entered a prescription for a particular medicine on patient room computer system 102. Upon noticing the prescription, the nurse may recognize that such a medicine is kept on-hand such that the nurse can begin the process of getting the medicine for the patient. Consequently, the patient does not have to wait until the visit is over to ask for such medicine. In another example, the nurse may notice that the healthcare professional is preparing to perform a specific test/procedure requiring specific supplies and/or assistance. Upon noticing such a need, the nurse can gather the supplies and/or prepare to assist the healthcare professional without the healthcare professional's specific request. Many other examples exist wherein the nurse of other monitoring person can provide improved service to a patient by simply understanding what the healthcare professional is doing during the patient visit. More details of the monitoring operation 1204 can be found in U.S. application Ser. No. 10/610,777, filed Jun. 30, 2003 and entitled "System and Method for Monitoring Patient Healthcare Information During a Visit, incorporated herein by reference for all that it discloses and teaches, filed concurrently herewith, and assigned to the Assignee of the present application.

Figure 2:
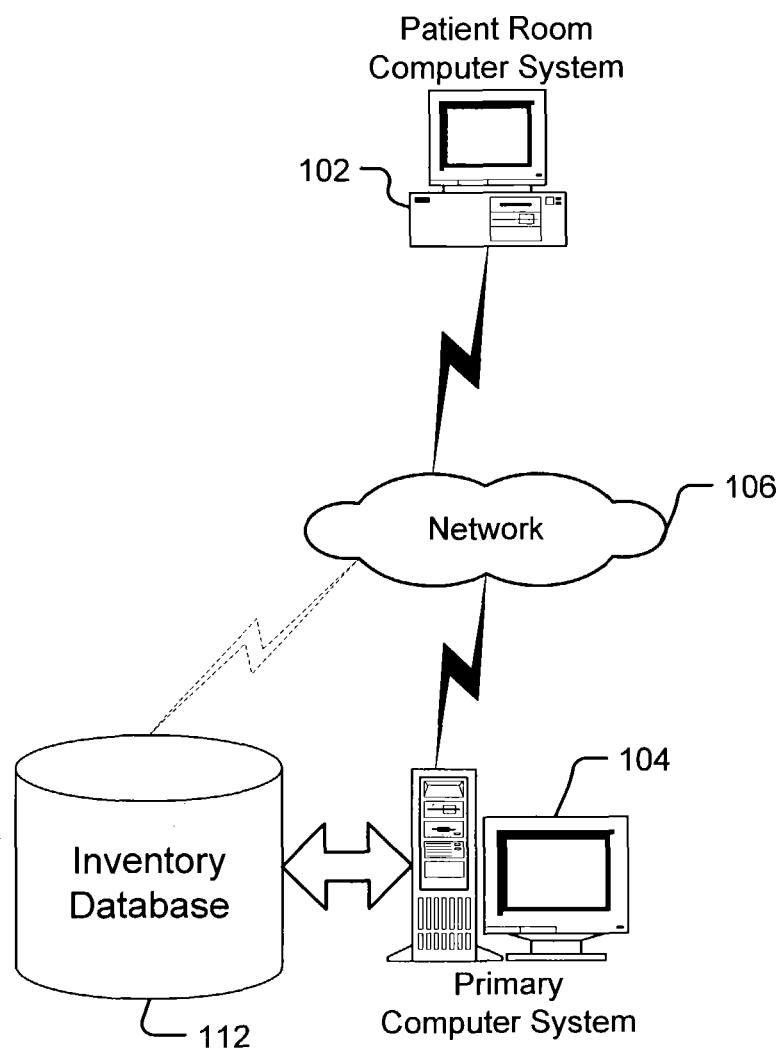
FIG. 2 is a block diagram of a particular embodiment of the system shown in FIG. 1, further comprising a connection to an electronic inventory system.

A particular embodiment of the system 100 shown in FIG. 1 involves connection of the primary computer system 104 to an inventory database 112, as shown in FIG. 2. The primary computer system 104 can therefore, determine whether certain items exist in local inventory. For instance, when a healthcare professional prescribes a particular medicine, the nurse may wish to provide some of the medicine to the patient upon completion of the visit. To that end, the primary computer system 104 may access the inventory database 112 to determine if the medicine is available. Moreover, upon determining that the medicine is available, the inventory database 112 may be updated as the nurse pulls some medicine from inventory. Such a process may occur relatively automatically, eliminating the need to manually check the inventory or separately accessing another computerized inventory program.

As may be understood, the inventory database may reside on the primary computer system 104, or it may be connected to another system and the primary computer system simply accesses the other system (not shown). The access may be direct or it may be indirect, e.g., such as through the network 106 or some other connection. Besides medicine, in other embodiments, the patient room computer system 102 has access to the inventory database for determining the availability of other items. Such access may provide a real time or automated basis for uploading and updating the inventory database 112 in relation to the medical supplies used during a visit, for example. That is, since the database may be accessed in real time, and managed electronically, the database system may further decrement the existing inventory and begin the process for ordering new supplies or medicine to re-stock the inventory.

Figure 3:
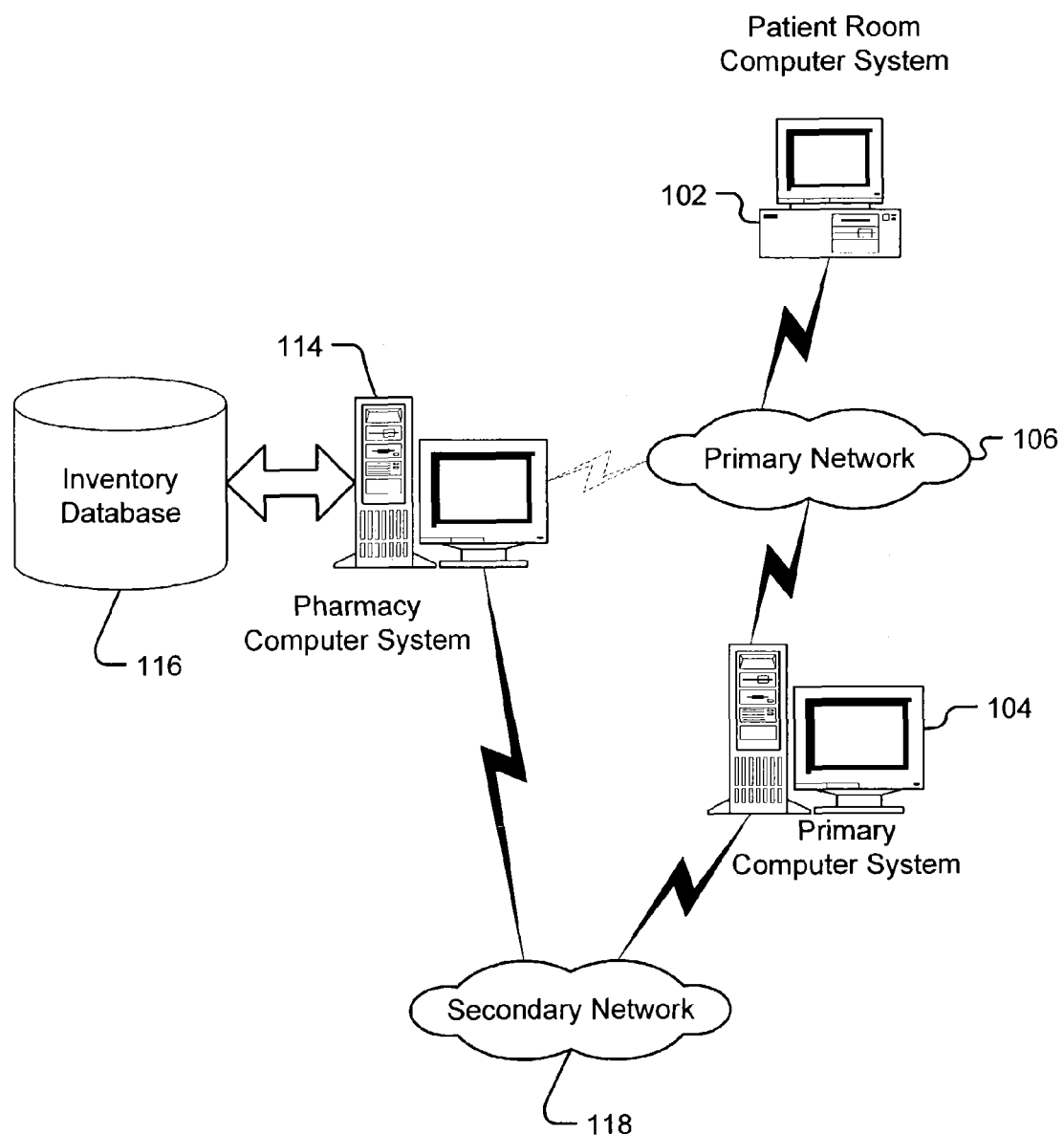
FIG. 3 is a block diagram of a particular embodiment of the system shown in FIG. 1, further comprising a connection to a pharmacy system, which may or may not include a connection to its own local inventory system.

In yet another particular embodiment (shown in FIG. 3), a pharmacy computer system 114 may communicate with or receive messages from the primary computer system 104. In this embodiment, should a particular medicine not be found locally, the computer system 104 may transmit a request to fill the prescription to a particular pharmacy computer system 114, which may have a pharmacy inventory database 116. The request may be transmitted via the primary network system 106, or through a secondary network connection 118. In this embodiment, the pharmacy has advanced notice of a particular prescription and can therefore plan accordingly by checking its database 116 and making sure the prescription can be filled. The pharmacy computer system 114 may further provide information back to the primary computer system 104 that further improves patient service, e.g., whether there is a generic version of the drug, whether the pharmacy of choice carries the medicine or has some on site, what the price will be for the medicine, the hours of operation for the pharmacy, etc. The patient may then receive this valuable information during check out, simplifying their next step in getting the medicine prescribed.

Figure 4:
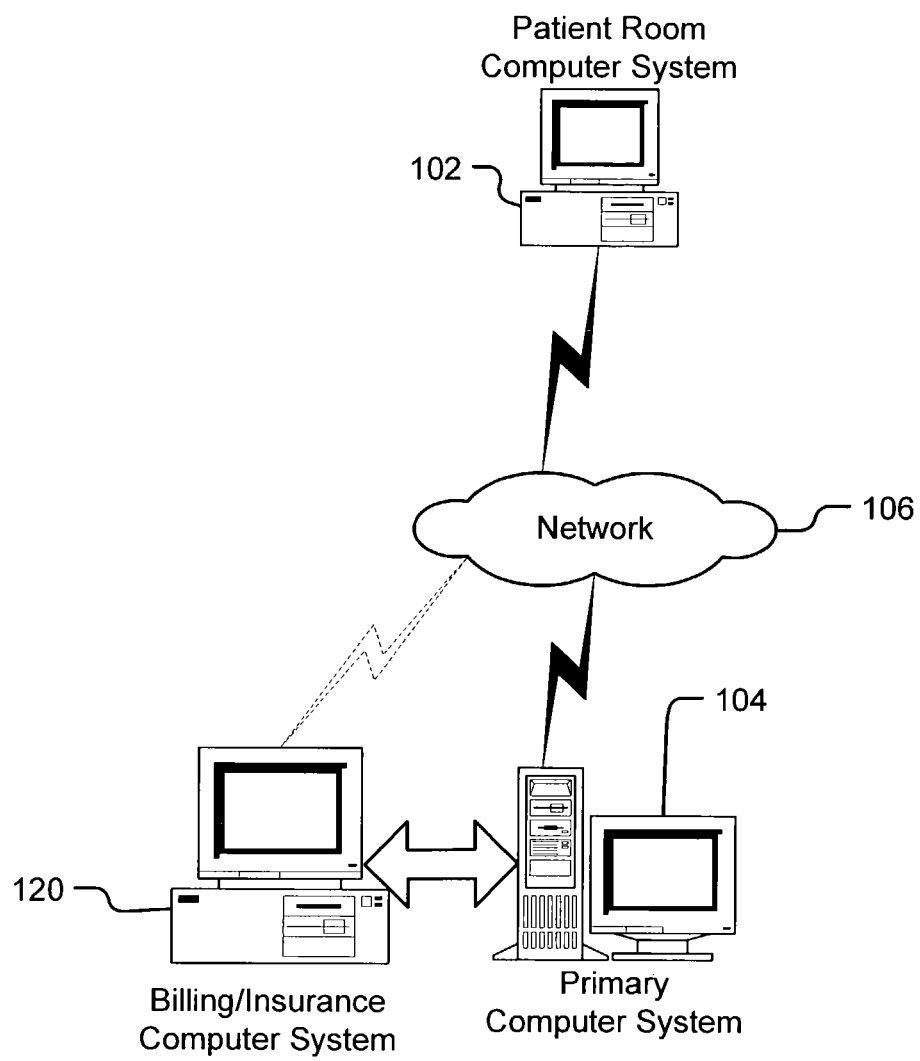
FIG. 4 is a block diagram of a particular embodiment of the system shown in FIG. 1, further comprising a connection to a billing system.

In yet another specific embodiment, the primary computer system 104 may be connected to a billing/insurance computer system or module 120, as shown in FIG. 4. The billing/insurance computer system 120 may be connected directly or indirectly with the primary computer system 104. In this embodiment, the primary computer system 104 can pass certain information received from the patient room computer system 102 to the billing computer system to improve the service provided to the patient. As an example, the billing computer system may be accessed to evaluate whether the insurance for the patient will pay for certain procedures prescribed by the healthcare professional. The system may further request pre-approval from the insurance company, relatively automatically. Further, an invoice may be generated to have available for the patient on check out, if necessary.

Figure 5:
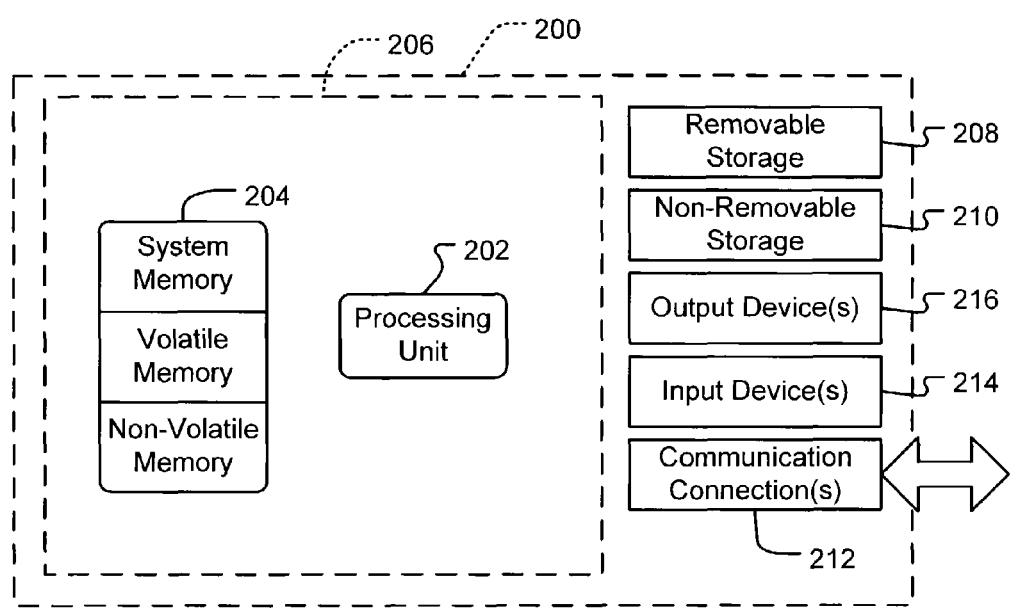
FIG. 5 illustrates a computer system that may be utilized in an embodiment of the present invention.

The computer systems, such as 102 and 104 may be represented by the computer system 200 shown in FIG. 5. The system 200 has at least one processor 202 and a memory 204. In its most basic configuration, computing system 200 is illustrated in FIG. 5 by dashed line 206 encompassing the processor 202 and the memory 204. Additionally, system 200 may also include additional storage (removable and/or non-removable) including, but not limited to, magnetic or optical disks or tape. Such additional storage is illustrated in FIG. 5 by removable storage 208 and non-removable storage 210. Computer storage media, such as memory 204, removable storage 208 or non-removable storage 210 includes volatile and nonvolatile, removable and non-removable media implemented in any method or technology for storage of information such as computer readable instructions, data structures, program modules or other data. Memory 204, removable storage 208 and non-removable storage 210 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by system 200. Any such computer storage media may be part of system 200. Depending on the configuration and type of computing device, memory 204 may be volatile, non-volatile or some combination of the two.

System 200 may also contain communications connection(s) 212 that allow the device to communicate with other devices. Additionally, system 200 may have input device(s) 214 such as keyboard, mouse, pen, voice input device, touch input device, etc. Output device(s) 216 such as a display, speakers, printer, etc. may also be included. All these devices are well known in the art and need not be discussed at length here.

Computer system 200 typically includes at least some form of computer readable media. Computer readable media can be any available media that can be accessed by system 200. By way of example, and not limitation, computer readable media may comprise computer storage media and communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer readable media.

Figure 6:
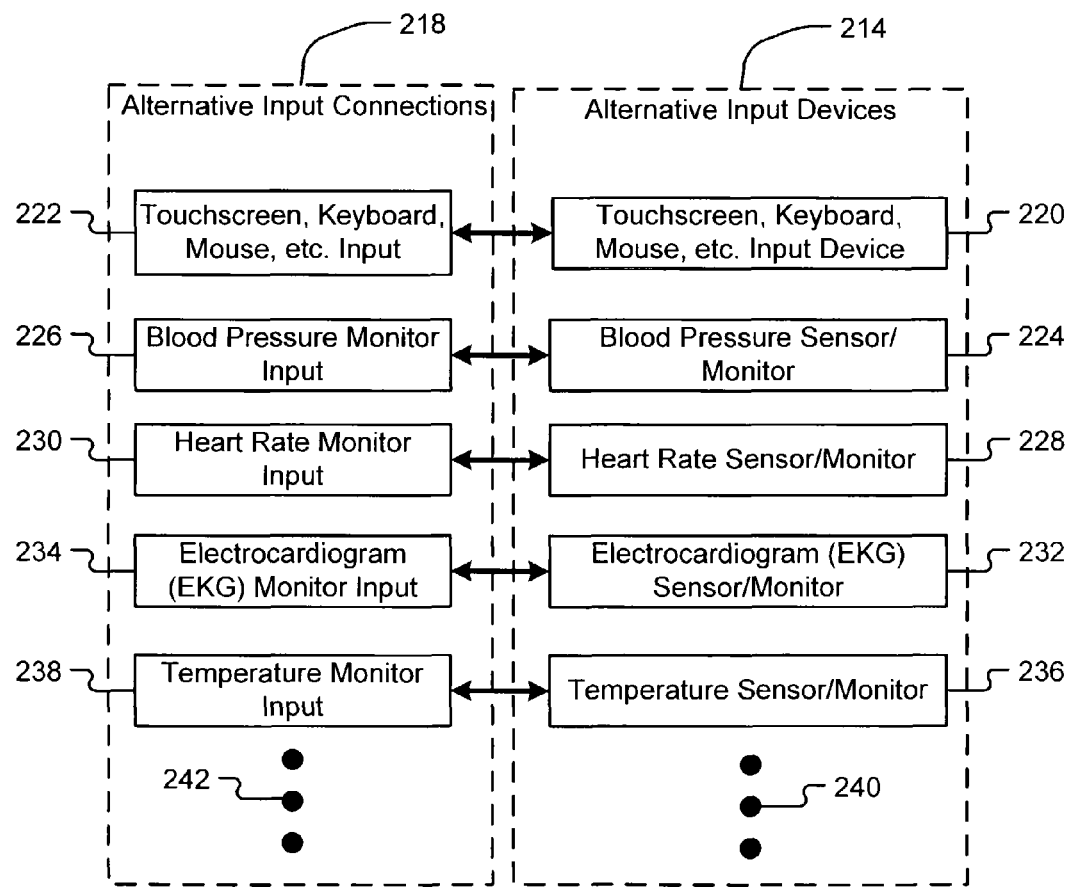
FIG. 6 illustrates a more detailed view of a particular computer as shown in FIG. 5 including automatic entry and remote entry capabilities and a particular embodiment.

As stated, the input devices 214 may include many different types of input devices. Some exemplary devices 214 are represented in FIG. 6. FIG. 6 also illustrates alternative input device connections 218. Although not shown in FIG. 5, the input connections 218 relate to the connection elements associated with the computer 200 and more particularly 206 to allow external input devices to communicate with the computer 206. For instance, the system 206 may receive input from more traditional devices 220 such as keyboard, mouse, pen, handwriting recognition, alphanumeric, voice input device, touch input device, etc. In order to receive input information from such devices, input connections 222 are used. The input connections 222 relate to the computer connections, whether serial, parallel, USB, AT, PS/2, etc. for receiving information from one of the devices 220.

In the embodiment shown in FIG. 6, other input devices are also used to provide input information to computer 206. For instance, a blood pressure sensor/monitor 224 may be connected to a blood pressure monitor input connection 226 for relatively automatically providing blood pressure information to the computer system 206. Similarly, a heart rate sensor/monitor 228 may be connected to a heart rate monitor input connection 230 for relatively automatically providing heart rate information to the computer system 206. Additionally, an electrocardiogram (EKG) sensor/monitor 232 may be connected to an electrocardiogram (EKG) monitor input connection 234 and a temperature sensor monitor 236 may be connected to a temperature monitor input connection 238 for relatively automatically providing EKG information and temperature information to the computer system 206, respectively. Furthermore, as may be understood, other items may also be used as indicated by ellipses 240 and 242.

In operation, during a visit, the healthcare professional retrieves a patient's chart on the patient room computer system, such as patient room computer system 102 shown in FIGS. 1-4. More details on automatic and semi-automatic downloading or accessing of patient chart information can be found in U.S. application Ser. No. 10/611,250 filed Jun. 30, 2003 and entitled "System and Method of Automatically Displaying Patient Information, now issued as U.S. Pat. No. 7,357,308, and incorporated herein by reference in its entirety.

Figure 7:
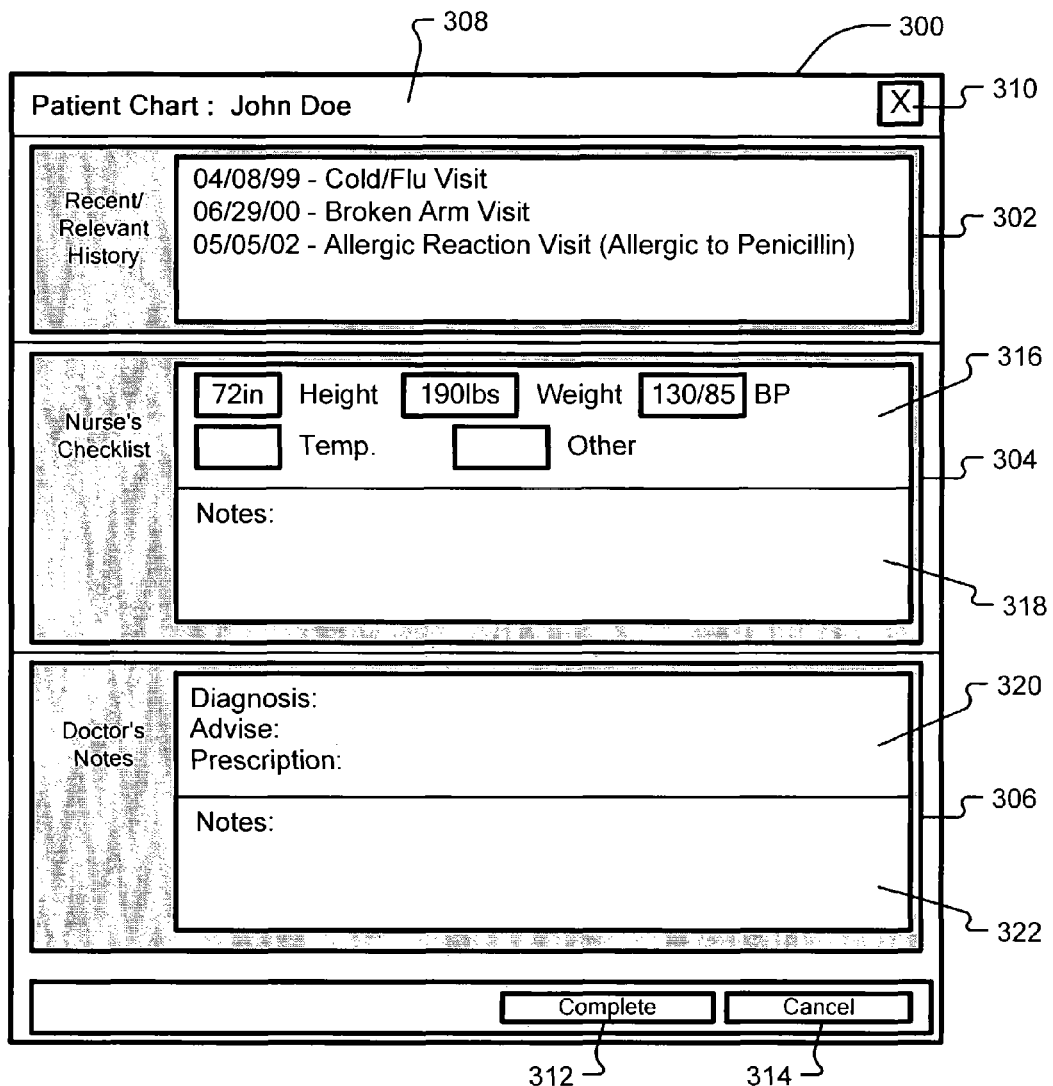
FIG. 7 illustrates a screen shot showing an exemplary graphical user interface for displaying and editing an electronic patient chart in accordance with an embodiment of the present invention.

A screen shot of an exemplary patient chart 300 is shown in FIG. 7. In this embodiment, the chart 300 is divided into at least three areas: a history area 302, a present-day checklist area 304, and a present diagnosis section 306. The chart also has a title bar 308 describing the patient and having a user-interface control 310 that allows the user to close the chart 300 when selected. The chart may further include user interface controls 312 and 314 that allow the user to update the chart, e.g., save the changes into memory using the "complete" control 312 or cancel and not save the changes using the "cancel" control 314.

In the history area 302, as shown in FIG. 7, many different historical items or information may be displayed. For instance a summary of recent visits may be displayed (as shown in FIG. 7). Alternatively, drug allergies may be shown, number of visits per year, recent types of prescribed medication, or almost any other type of historical data may be displayed. The area 302 may also include user-interface controls (not shown) to scroll through historical items or to select certain types of items to display. In an embodiment, the historical area may not be edited such that no accidental changes can be made.

The present-day checklist area 304, titled "Nurse's Checklist" includes two portions, a checklist portion 316 and a notes section 318. The checklist portion 316 provides text boxes for entering information related to the patient on the day of the visit. That is, when visiting a doctor or another health professional, a nurse typically gathers information about the patient, such as height, weight, blood pressure (BP), temperature and/or potentially other information. The area 304 provides a convenient means for entering the information and a checklist for reminding the nurse of the various items to be tested and/or information to be gathered. It is foreseeable that this area would be customizable to a particular practice depending on preferences of a particular healthcare professional. For instance, a podiatrist would care about different information than a general practice physician and thus the items in area 316 may be different for different healthcare professionals.

In addition to checklist portion 316, the nurse can enter notes to the healthcare professional by editing the notes section 318. That is, during a typical visit, the nurse visits with the patient first, gathering information in area 316 and to find out the purpose of the visit. The nurse can quickly make a note of the purpose of the visit, e.g., "pain in stomach" or "high temperature", etc. Subsequently, the healthcare professional is able to quickly ascertain the issues by reading the notes section 318. Of course, any other relevant notes may be entered into section 318.

The third area of the chart 300 relates to the healthcare professional's area 306. In the example shown in FIG. 7, the area 306 is titled "Doctor's Notes" and is divided into two sections, diagnosis area 320 and notes area 322. The diagnosis area 320 is generally reserved for the healthcare professional's specific diagnosis and advice given to the patient, as well as any prescriptions written for the patient. This information may become part of the permanent chart for the patient. The healthcare professional also has a notes section 322 for taking notes regarding the visit. This information may or may not become part of the permanent chart for the patient.

Figure 8:
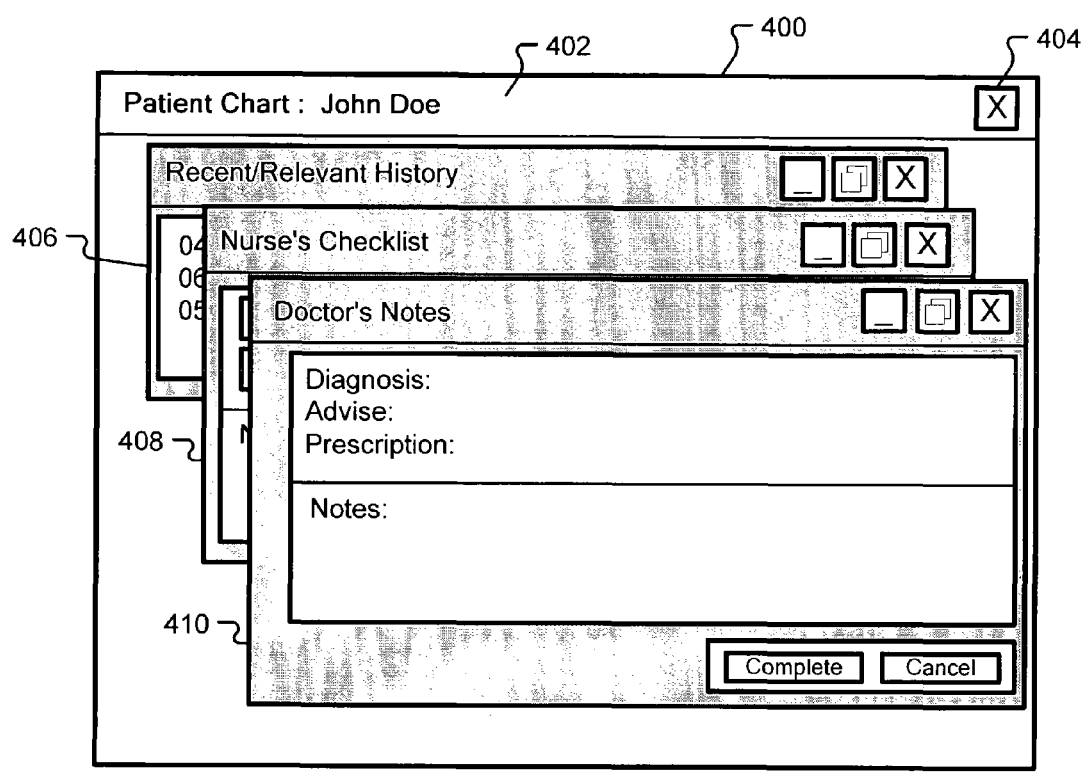
FIG. 8 illustrates a screen shot showing another exemplary graphical user interface for displaying and editing an electronic patient chart using a plurality of window controls in accordance with another embodiment of the present invention.

In another embodiment, different portions of a patient chart, such as chart 400, are presented as separate window elements, as shown in FIG. 8. Chart 400 incorporates a title bar 402 and a user-interface control element 404 to close the chart when selected. The chart 400 also has a plurality of sub-window elements, such as elements 406, 408 and 410. In this example the sub-window elements 406, 408 and 410 correspond to the different chart areas 302, 304 and 306 associated with chart 300 shown in FIG. 7. That is, element 406 is a relevant history window element that comprises similar information as relevant history area 302. Also, the window element 408 comprises similar information as the portion 304, including a checklist area and a notes area. Further, window element 410 is similar to the portion 306 shown and described in conjunction with FIG. 7.

As discussed above, FIGS. 7 and 8 illustrate examples of potential screens or graphical user interface elements that may be implemented in an embodiment of the present invention as part of the overall user interface. The purpose of these user interface elements is to display relevant information in a meaningful manner as well as provide a meaningful way to enter new, updated patient information so that it can be stored as part of the patient's medical chart and thus medical history. As may be appreciated, many other user interface elements, including but not limited to, pop up screens, menus, pop up menus, control elements, etc. may be designed to achieve this function. Consequently, FIGS. 7 and 8 are intended to be mere examples of electronic versions of patient chart information and the user interfaces for reading and editing the same.

The logical operations of the various embodiments of the present invention may be implemented (1) as a sequence of computer implemented steps running on one or more computing systems and/or (2) as interconnected machine logic modules within the computing systems. Accordingly, the logical operations making up embodiments of the present invention described herein are referred to variously as operations, acts, steps or modules as shown and described more fully below with respect to FIGS. 9-12.

Figure 9:
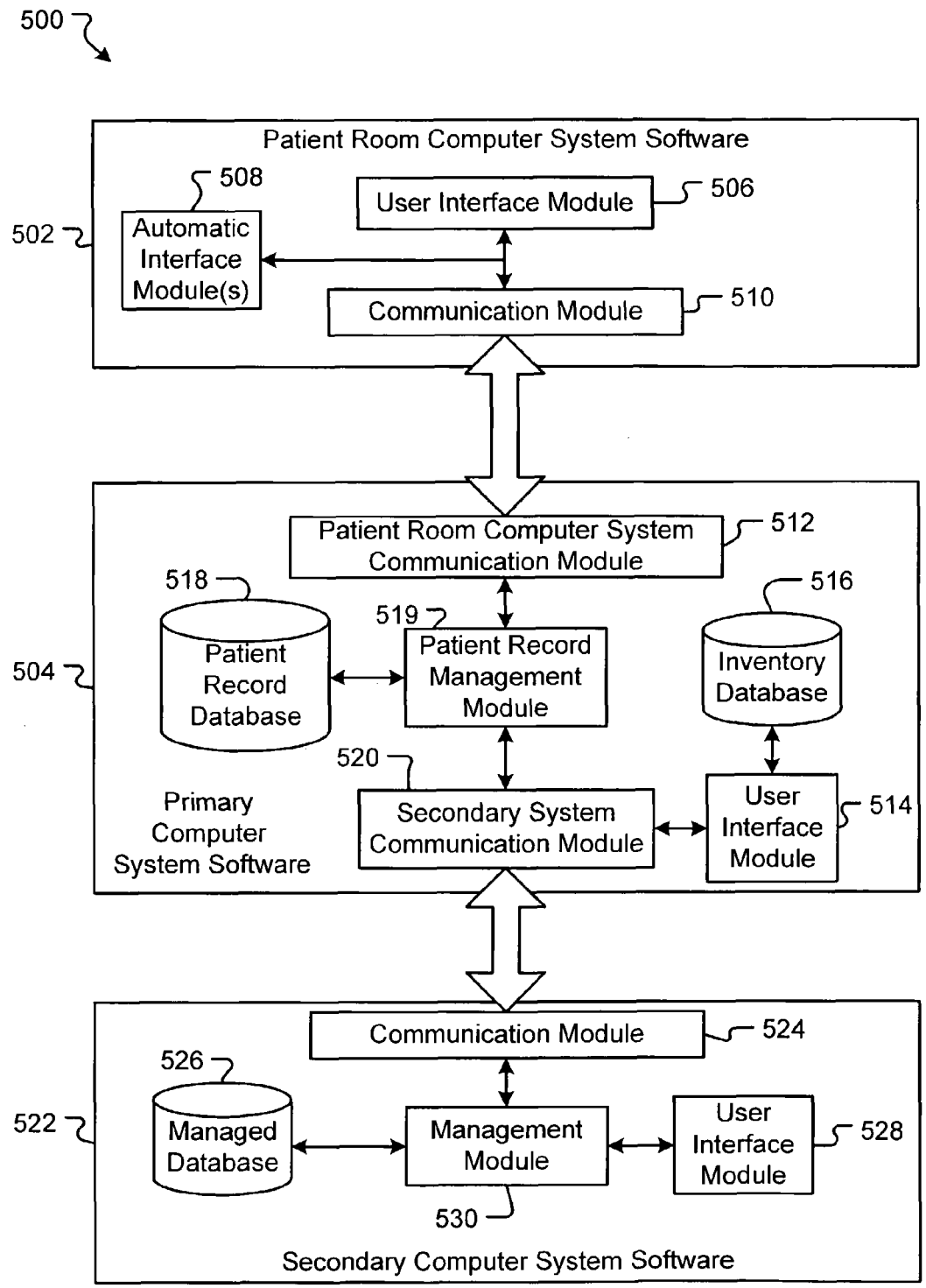
FIG. 9 illustrates software elements in an embodiment of the present invention.

FIG. 9 illustrates a software/hardware environment 500 incorporating aspects of the present invention. The environment 500 includes separate modules that perform functional operations in accordance with those aspects and wherein the modules are communicably connected as needed to perform certain functions as shown in FIG. 9. In general, the environment 500 comprises a patient room computer system or layer of software 502 and a primary computer system or layer of software 504, which, in one embodiment correspond respectively to the patient room computer system 102 and the primary computer system 104 shown in FIG. 1. The patient room computer system software 502 communicates with the primary computer system software 504 to store patient charts and, in one environment, to simultaneously display a patient chart during a patient visit. The primary computer software 504 accesses, in an embodiment, inventory databases, patient record databases, and, in other embodiments, other computer systems to provide information to the patient room computer system software and to manage other patient needs.

The patient room computer system software layer 502 has a user interface module 506 to both provide information to a user, e.g., through a monitor, speakers or some other device and to receive data from a user, e.g., through a keyboard, touch screen, etc. The different types of input devices are described above in conjunction with FIGS. 5 and 6. The user interface module 506 provides the software functionality to receive data and display the same to the user.

The patient room computer system software layer 502 also has an automatic interface module or modules 508. These modules provide software support for the automatic data entry provided from some other system, such as the systems shown and described in conjunction with FIG. 6. For instance, in an embodiment, the blood pressure monitor may be connected to a computer system for reading, storing and displaying blood pressure. This monitor may be connected to the patient room computer system as discussed above in conjunction with FIG. 6 to transfer blood pressure information to the patient room computer system. When connected, the patient room computer software modules 508 provide the software communication support to allow the transfer of this information to the patient room computer system. Other modules 508 may be implemented to receive information from other sensors or monitors as shown in FIG. 6.

In one embodiment, the user interface module 506 receives data from the user and stores the information locally. In another embodiment, the information is transmitted to the software system 504 for storage on the primary computer software system. In order to transmit the information to the primary computer system software layer 504, the patient room computer system software layer 502 has a communication module 510. The communication module 510 communicates with communication module 512 located on the primary computer system software layer. In an embodiment, the communication modules 510 and 512 communicate over an intranet. In yet another embodiment, the modules 510 and 512 communicate over the Internet, or some other network configuration. In other embodiments the communication connection between 510 and 512 is wireless, while other embodiments employ non-wireless technology.

In addition to the communication module 512, the primary computer system software layer may incorporate many other software elements. For example, the layer 504 has a user interface module 514. The user interface module 514 is similar to the user interface module 506 in that it provides software support for receiving data from a user and displaying or providing information to the user. The actual module 514 may differ from module 506 in that the systems may have different user interface elements, e.g., a touch screen instead of a keyboard, or a mouse instead of a pen device, etc.

The software layer 504 also has a patient record database 518. The patient record database includes the various patient charts as well as other patient-related information. In operation, the healthcare professional accesses the patient chart, stored in the database 518, and upon making changes, stores the chart back to the record database 518. In order to manage the patient records, the system 504 uses a patient records management module 519. The management module 519 relates to the applications or other program elements used and accessed by a user to store, retrieve and otherwise manage the patient records stored in database 518.

Another functional module that might exist on the primary computer system software layer 504 relates to an inventory database 516. The inventory database may house information related to various items kept in local inventory, e.g., medicine, samples, medical supplies, etc. A user may access such information though the user interface module 516. Alternatively, the inventory database may be accessed through a secondary system communication module 520. In this situation, the secondary system module 520 may receive a request to check the inventory, and in response, the secondary system control module accesses the inventory application/database 516 located on the primary computer system.

In an alternative embodiment the secondary system communication module 520 communicates with a separate, secondary computer system software layer 522, and in particular with a communication module 524 located on the secondary system. The secondary computer system software may be implemented as an electronic or computerized inventory application, a billing application, a scheduling system, or some other administrative system. In yet other embodiments, the secondary computer system may relate to a pharmacy system located in a separate location than the primary computer system that receives requests for information regarding medicines located in that pharmacy, e.g., whether such medicines are in stock, how much such medicines cost, etc. As such, the secondary system incorporates an inventory database 526 and a user interface module 528 to aid in the administration of these requests from the primary computer, system software 504. Additionally, in order to manage the inventory database 526, the system 522 uses a management module 530. The management module 530 relates to the applications or other program elements used and accessed by a user to store, retrieve and otherwise manage the inventory records stored in database 526.

Communications between the primary computer system 504 and the secondary computer system 522 may require some level of security. That is, when the primary computer system 504 requests information from the secondary computer system 522, the secondary computer system 522 may need to determine whether the primary computer system 504 is authorized to access and/or receive the requested information. This level of security may be handled relatively automatically if the computer systems have communicated in the past using methods known in the art. Alternatively, a healthcare professional, such as the nurse operating the primary computer system 504 may be required to enter authorization information, such as a user name and password to access the requested information.

Figure 10:
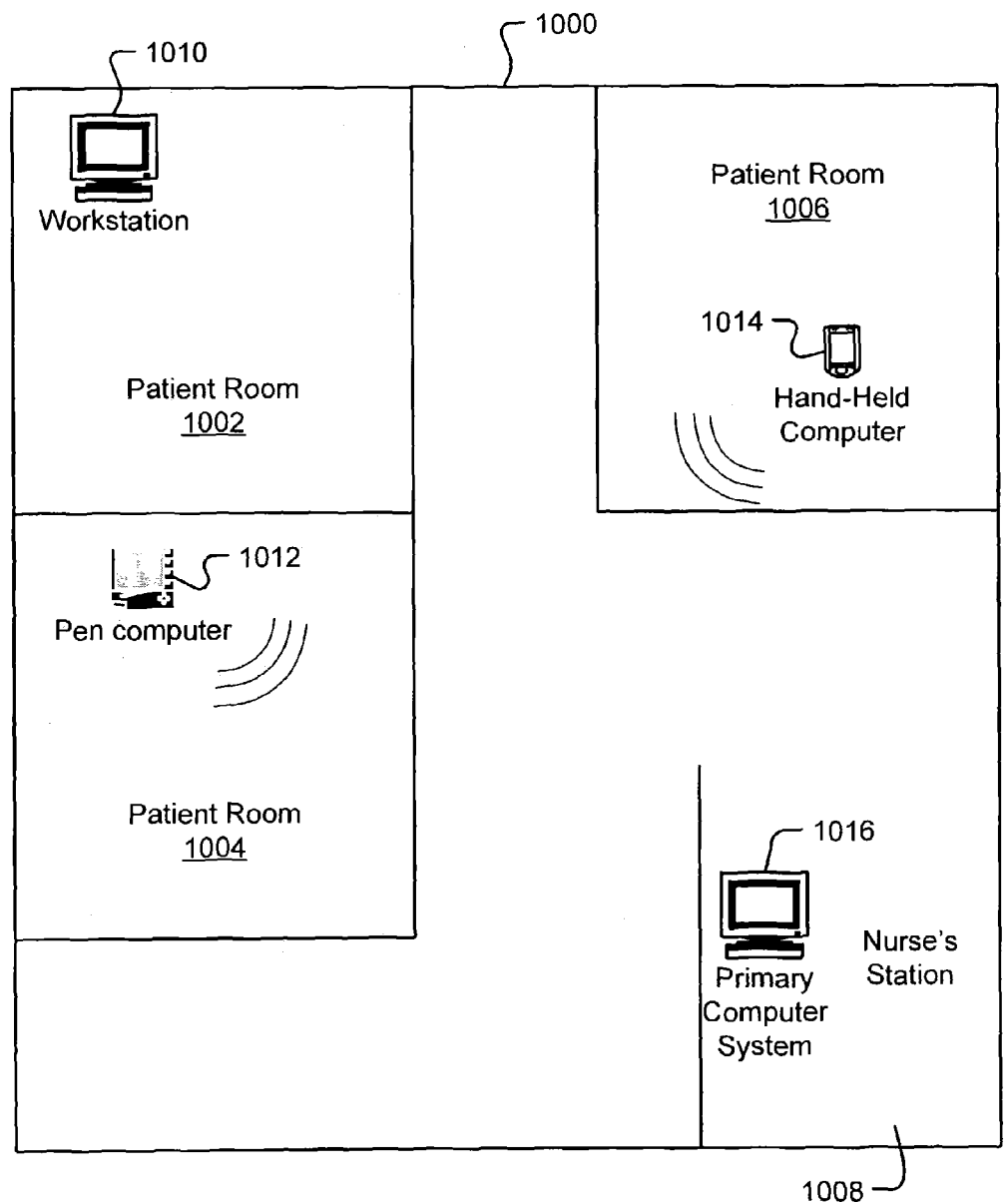
FIG. 10 illustrates an exemplary healthcare professional's office implementing concepts of the present invention, including different types of patient room computer systems.

An exemplary healthcare professional's office 1000 utilizing aspects of the present invention is shown in FIG. 10. Although described as an office, is should be recognized that this may relate to a portion of a hospital, clinic or some other patient care facility. In particular, the office 1000 includes three patient rooms 1002, 1004 and 1006. The patient rooms are separate meeting rooms where the healthcare professional will meet with different patients. The office 1000 also has a nurse's station 1008. The station 1008 may have many different elements, including filing cabinets, medicine cabinets, etc. The nurse's station 1008, in an embodiment, has one or more nurses or other support staff present during patient visits.

In the exemplary environment shown in FIG. 10, located inside each of the patient rooms 1002, 1004 and 1006 is a computer system. As shown in FIG. 10, the computer may be in the form of a workstation 1010 (patient room 1002), a pen computer 1012 (patient room 1012), or a hand-held computer system 1014 (patient room 1006). Each of the different computer systems 1010, 1012 and 1014 communicate with a primary computer system 1016. In the embodiment shown in FIG. 10, the primary computer system is located in the nurse's station 1008. The different computers 1010, 1012 and 1014 are shown in FIG. 10 to illustrate that many different types of computer systems may be used in accordance with the present invention. Indeed, many other types of computer systems that are not shown may also be used as patient room computer systems, as long as it communicates with the primary computer system to send and receive patient record or chart information.

As may be understood, the computer system 1010 represents an example of a patient room computer system 102 shown in FIGS. 1-4. As shown, the computer 1010 is a workstation designed to remain within the patient room 1002, i.e., it is not mobile. The workstation 1010 may be used to enter information during a patient visit and to display a patient's chart to a user, among other things, as discussed above. In this embodiment, the workstation 1010 is connected via wires to the primary computer system 1016, i.e., it is hard-wired to the primary computer system 1016. In another embodiment, the workstation 1010 may be connected to an intermediate server computer system (not shown). In such an embodiment, the primary computer system 1016 would also be connected to the server computer system (not shown) such that the workstation 1010 and the primary computer system 1016 communicate with each other.

Office 1000 also demonstrates two other types of patient room computer systems 102, i.e., pen computer system 1012 and hand-held computer system 1014. The pen computer system 1012 relates to a computer system that has different input functionality, such as a pen input instead of, or in addition to, a more traditional keyboard/mouse input system. The hand-held computer system 1014 relates to a portable computer system that a healthcare professional may carry from room to room. The hand-held computer system may have a touch screen and/or other types of input/output functionality that is different from other patient room computer systems 1010 and 1012.

One difference between the systems 1012 and 1014 from the workstation 1010, as shown in FIG. 10, is that the systems 1012 and 1014 are meant to illustrate the use of wireless computer systems that communicate with the primary computer system. As such, the pen computer system 1012 and hand-held computer system 1014 transmit information in a wireless manner to a receiver (not shown) which then communicates the information to the primary computer system 1016. The receiver may be located in or on the primary computer system 1016 or as part of a server system (not shown). Importantly, in an embodiment, the primary computer system also has wireless capabilities to transmit information to the pen computer 1012 and/or the hand-held computer system 1014. As a result, the systems 1012 and 1014 receive important information related to a patient from the primary computer system when necessary.

In an embodiment, the systems 1010, 1012 and 1014 communicate with the primary computer system 1016 via a local intranet system. However, in other embodiments, the systems 1010, 1012 and 1014 may communicate with the primary computer system 1016 via a wide area network, and in some cases the network is the Internet. As such, a health professional may visit a patient in another building, such as a hospital, or at their home, and the health professional may communicate with the primary computer system 1016 to both transmit information and receive information.

Figure 11:
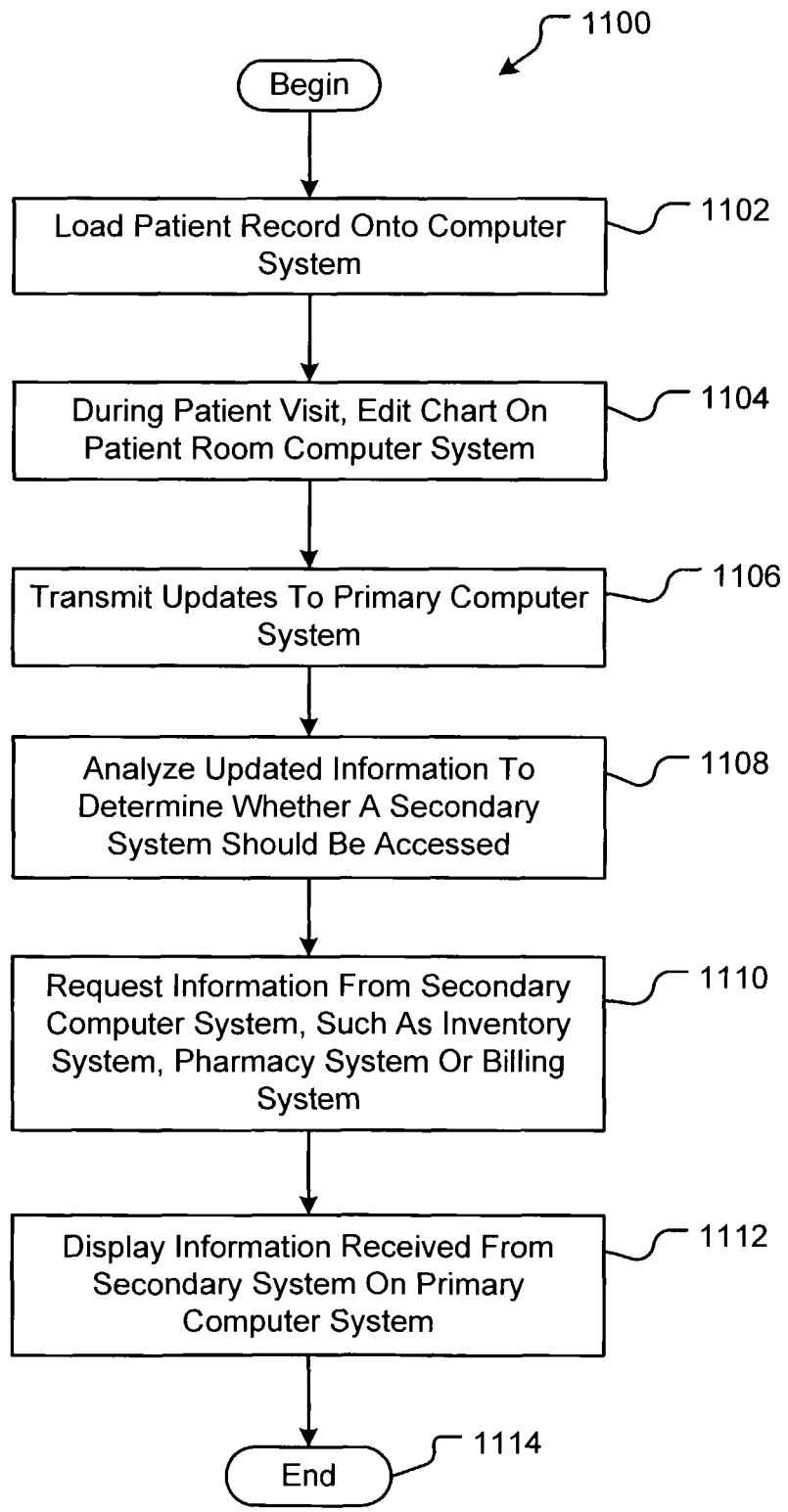
FIG. 11 illustrates a flowchart of functional operations related to entering information into a patient chart with respect to an embodiment of the invention.

FIG. 11 illustrates a flowchart of functional operations related to entering information into a patient chart and displaying the same on a primary computer system. Initially, flow 1100 begins with load operation 1102. Load operation loads patient record information onto a patient room computer system, such as patient room computer system 102 shown and described in conjunction with FIGS. 1-4 above. In an embodiment, before the patient record or chart can be loaded on the patient room computer system 102, the chart must be entered onto a primary computer system, such as system 104 shown and described above in conjunction with FIGS. 1-4. Many known methods of entering data may be implemented when initially loading the information onto the primary computer system, e.g., typing the information or scanning the information may be exemplary data entry methods.

Once a patient's chart has been loaded on the primary computer system, load operation 1102 loads the chart on the patient room computer system, such as system 102. In an embodiment, a healthcare professional uses the patient room computer system 102 to access the chart. Such a process may involve the transmission of a request to the primary computer system, including the type of information requested, e.g., a patient's chart, and the name of the patient. In response, the primary computer system may require some identification information, such as a login name and password for security purposes. Upon providing the identification information, the primary computer system transmits the requested information to the patient room computer system, completing load operation 1102. At this time, the healthcare professional has access to the requested patient's chart. Although flow 1100 relates primarily with the loading of a single patient record onto a patient room computer system, in practice many different patient records may be loaded onto the computer system during a session and later recalled individually when needed.

Next, edit operation 1104 edits the patient's chart. During a typical scenario, the healthcare professional edits the chart during the patient's visit. Although this step may occur following the visit, such late entry reduces the ability to improve the efficiency of the visit as information will not be shared with other computer systems during the visit. Therefore, it is contemplated that this information will most likely be entered during the visit.

In the embodiment shown in FIG. 11, upon entry of information into the patient's chart, transmit operation 1106 transmits the update information to the primary computer system. Further, in this embodiment, upon receiving the information, analyze operation 1108 automatically analyzes the update information to determine if additional information from a secondary computer system should be requested. Analyze operation 1108 may parse the update information to determine whether a predetermined type of update has occurred. For example, analyze operation 1108 may test the update information to determine if a new prescription has been entered. Alternatively, analyze operation may determine whether a new procedure has been prescribed, thereby requiring medical equipment of supplies. Yet other predetermined information may also lead to contacts with other computer systems, such as information regarding new appointments such that a calendar system may be contacted or information regarding the tests and procedures preformed or prescribed such that a billing and/or insurance computer system may be contacted.

Once analyze operation 1108 determines that a secondary computer system should be contacted, request operation 1110 requests information from the predetermined secondary system. Request operation 1110 relates to the general communications between the primary computer system and the secondary computer system. Given that the secondary computer system is being contacted as a result of an update to a patient chart, it is contemplated that the primary computer system is attempting to manage some particular issue for the patient. Moreover, in this situation, it would be rare for the primary computer system to actually send some information to a secondary application or computer system without receiving any information in response. However, it is contemplated within this invention that the request for information 1110 includes a request to notify one or more other systems or applications of an update, such as an inventory system may be notified that a predetermined amount of medicine (based on the updated patient chart information) should be decremented from the inventory. In a more typical scenario, the inventory system would be accessed and information regarding the available inventory would be sent to the primary computer system in response to the specific request.

As discussed above with respect to FIG. 9, the communications between the primary computer system and the secondary computer system may require an initial step (not shown) of authorizing the primary computer system. The authorization step may occur automatically, or the attending nurse may be required to enter authorizing/identifying information to begin the requesting process.

Upon receiving the requested information, display operation 1112 displays such information to allow a healthcare professional working with the primary computer system to evaluate the information. From this, the healthcare professional can determine any other necessary operations that must be performed, including but not limited to, accessing other computer system or applications, notifying the attending doctor of particular issues, etc.

Following display operation, flow 1100 ends at end operation 1114.

Figure 12:
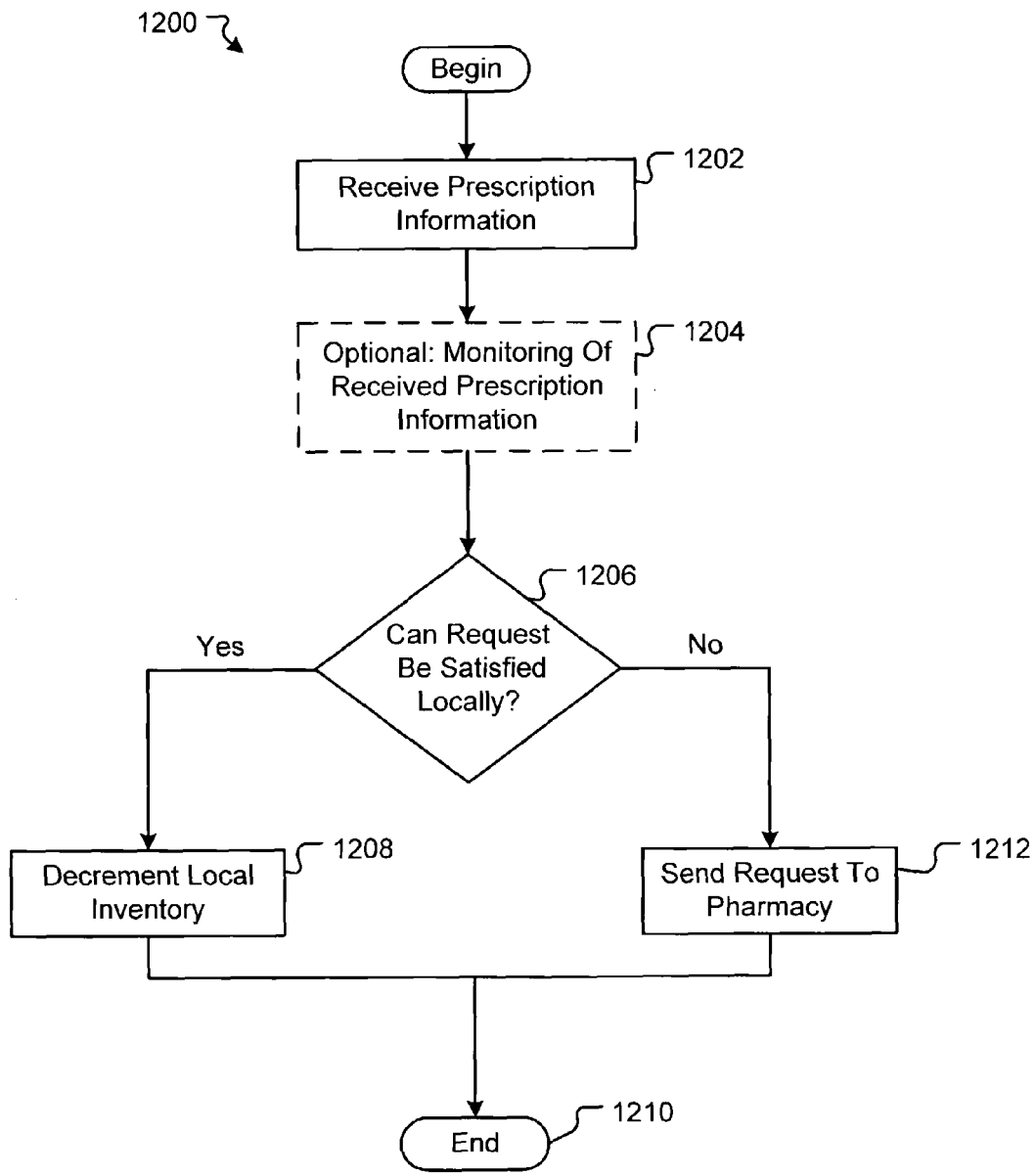
FIG. 12 illustrates a flowchart of functional operations related to administering an entered prescription for a patient into a patient chart in accordance with an embodiment of the present invention.

FIG. 12 illustrates a flowchart of functional operations related to entering a prescription for a patient into a patient chart in accordance with an embodiment of the present invention. Initially flow 1200 begins with receive prescription information operation 1202. The receive operation 1202 relates to the reception of a patient chart update operation shown and described above with respect to FIG. 11. That is, when a healthcare professional enters a new medical prescription into the patient's chart, such as in a patient room computer system displayed chart, the information is transmitted to the primary computer system. Receive operation 1202 relates specifically to the reception of such prescription information.

Upon receiving the prescription information, an optional monitoring operation 1204 may occur. Monitor operation relates to the simultaneous display of the prescription information on the primary computer system such that a nurse or other healthcare professional can monitor the information. Alternatively, the monitoring of the prescription information may be done automatically using a computerized method of parsing the medical history of the patient and determining whether the prescribed medicine is safe or proper for the particular patient. Automatic monitoring requires a predetermined table or chart of suitable medicines give the patient's diagnosis, medical history, age, weight, etc. Through the monitoring operation, errors may be determined quickly in order to avoid potential harm to the patient. More details of the monitoring operation 1204 can be found in U.S. application Ser. No. 10/610,777 filed Jun. 30, 2003 and entitled "System and Method for Monitoring Patient Healthcare Information During a Visit, previously incorporated herein by reference.

Following the optional monitoring operation 1204, test operation 1206 tests to see if the prescription request can be satisfied locally. That is, many healthcare facilities carry a significant amount of medicine in their local inventory. The test operation 1206 tests the local inventory database to see if such medicine is available. If so, flow branches "yes" to decrement operation 1208, which decrements the local inventory database. That is, decrement operation 1208 updates the local inventory to reflect the use of this particular prescription. Consequently, future requests for that medicine are subject to this particular request. Following decrement operation 1208, flow ends at 1210.

On the other hand if test operation 1206 determines that the prescription request cannot be satisfied locally, flow branches "no" to send operation 1212. Send operation 1212 sends a request to a pharmacy to begin processing the prescription at the pharmacy location. Following the send operation 1212, flow ends at 1210.

Using the above methods and system, secondary systems can be accessed automatically, which eases the administrative processes involved with managing patient care. Indeed, several secondary systems can be accessed automatically to provide the patient information regarding prescriptions, scheduling, billing and others upon leaving the healthcare facility. Since these other systems are accessed using the primary computer system, stemming directly from the data entered by the healthcare professional contemporaneously with the patient visit such that there is a reduced chance for error.

It will be clear that the present invention is well adapted to attain the ends and advantages mentioned as well as those inherent therein. While a presently preferred embodiment has been described for purposes of this disclosure, various changes and modifications may be made which are well within the scope of the invention. Numerous other changes may be made which will readily suggest themselves to those skilled in the art and which are encompassed in the spirit of the invention disclosed and as defined in the appended claims.

What is claimed is:

1. A method, comprising:
wirelessly receiving, by a mobile device, a wireless room identification signal wirelessly transmitted from a room transceiver, the wireless room identification signal identifying a wireless network and the room transceiver;
establishing, by the mobile device, electronic communication via the Internet with a server;
automatically wirelessly transmitting, from the mobile device, an electronic request addressed to the room transceiver upon a receipt of the wireless room identification signal, the electronic request requesting an electronic patient chart, and the electronic request specifying the room transceiver;
routing, by the room transceiver, the electronic request via the Internet to the server, the server associated with an Internet Protocol address;
querying, by the server, an electronic database for the room transceiver specified by the electronic request, the electronic database electronically associating electronic patient charts and transceivers including the room transceiver specified by the electronic request;
retrieving, by the server, the electronic patient chart identified by the electronic database that is electronically associated with the room transceiver;
routing, from the server, the electronic patient chart via the Internet to the room transceiver for a wireless transmission via the wireless network to the mobile device;
receiving, at the mobile device, the electronic patient chart in response to the electronic request automatically wirelessly transmitted from the mobile device upon a receipt of the wireless room identification signal;
automatically displaying, by the mobile device, the electronic patient chart in response to the receipt of the wireless room identification signal;
linking, via the Internet, a display of the electronic patient chart at the mobile device with another display associated with the server such that the electronic patient chart is simultaneously displayed by both the mobile device and by the server;
monitoring, by the server, the electronic patient chart for an entry of a medicinal prescription at the mobile device;
sending, from the server, an electronic query to an inventory database for an inventory associated with the medicinal prescription; and
decrementing, by the server, the inventory to reflect the entry of the medicinal prescription in the electronic patient chart displayed by the mobile device.

2. The method of claim 1, further comprising comparing the electronic patient chart to the inventory.

3. The method of claim 1, further comprising comparing the electronic patient chart to a prescription in a prescription database.

4. The method of claim 1, further comprising comparing the electronic patient chart to a schedule in a scheduling database.

5. The method of claim 1, further comprising receiving the inventory associated with the medicinal prescription.

6. The method of claim 5, further comprising receiving information associated with pharmacy locations stocking the medicinal prescription.

7. The method of claim 5, further comprising receiving information associated with pickup times for the medicinal prescription.

8. The method of claim 1, further comprising determining an insurance coverage associated with the medicinal prescription.

9. The method of claim 1, further comprising ordering supplies to restock the inventory.

10. A system, comprising:
a hardware processor; and
a memory device, the memory device storing instructions, the instructions when executed causing the hardware processor to perform operations, the operations comprising:
wirelessly receiving a wireless room identification signal wirelessly transmitted from a room transceiver, the wireless room identification signal identifying a wireless network and the room transceiver;
establishing electronic communication via the Internet with a server;
automatically wirelessly transmitting an electronic request addressed to the room transceiver upon a receipt of the wireless room identification signal, the electronic request requesting an electronic patient chart, and the electronic request specifying the room transceiver;
routing the electronic request via the Internet to the server, the server associated with an Internet Protocol address;
querying an electronic database for the room transceiver specified by the electronic request, the electronic database electronically associating electronic patient charts and transceivers including the room transceiver specified by the electronic request;
retrieving the electronic patient chart identified by the electronic database that is electronically associated with the room transceiver;
routing the electronic patient chart via the Internet to the room transceiver for a wireless transmission via the wireless network to the mobile device;
receiving the electronic patient chart in response to the electronic request automatically wirelessly transmitted from the mobile device upon a receipt of the wireless room identification signal;
automatically displaying the electronic patient chart in response to the receipt of the wireless room identification signal;
linking a display of the electronic patient chart at the mobile device with another display associated with the server such that the electronic patient chart is simultaneously displayed by both the mobile device and by the server;
monitoring the electronic patient chart for an entry of a medicinal prescription at the mobile device;
sending an electronic query to an inventory database for an inventory associated with the medicinal prescription; and
decrementing the inventory to reflect the entry of the medicinal prescription in the electronic patient chart displayed by the mobile device.

11. A memory device storing instructions which when executed cause a hardware processor to perform operations, the operations comprising:
wirelessly receiving a wireless room identification signal wirelessly transmitted from a room transceiver, the wireless room identification signal identifying a wireless network and the room transceiver;
establishing electronic communication via the Internet with a server;
automatically wirelessly transmitting an electronic request addressed to the room transceiver upon a receipt of the wireless room identification signal, the electronic request requesting an electronic patient chart, and the electronic request specifying the room transceiver;
routing the electronic request via the Internet to the server, the server associated with an Internet Protocol address;
querying an electronic database for the room transceiver specified by the electronic request, the electronic database electronically associating electronic patient charts and transceivers including the room transceiver specified by the electronic request;
retrieving the electronic patient chart identified by the electronic database that is electronically associated with the room transceiver;
routing the electronic patient chart via the Internet to the room transceiver for a wireless transmission via the wireless network to the mobile device;
receiving the electronic patient chart in response to the electronic request automatically wirelessly transmitted from the mobile device upon a receipt of the wireless room identification signal;
automatically displaying the electronic patient chart in response to the receipt of the wireless room identification signal;
linking a display of the electronic patient chart at the mobile device with another display associated with the server such that the electronic patient chart is simultaneously displayed by both the mobile device and by the server;
monitoring the electronic patient chart for an entry of a medicinal prescription at the mobile device;
sending an electronic query to an inventory database for an inventory associated with the medicinal prescription; and
decrementing the inventory to reflect the entry of the medicinal prescription in the electronic patient chart displayed by the mobile device.

* * * * *